US011241562B2

(12) United States Patent
Jones et al.

(10) Patent No.: US 11,241,562 B2
(45) Date of Patent: Feb. 8, 2022

(54) INGESTIBLE DEVICE WITH RELATIVELY LARGE PAYLOAD VOLUME

(71) Applicant: Progenity, Inc., San Diego, CA (US)

(72) Inventors: Mitchell Lawrence Jones, La Jolla, CA (US); Russell B. Ford, Palo Alto, CA (US); Edward G. Solomon, Menlo Park, CA (US); Jeffrey A. Shimizu, Poway, CA (US)

(73) Assignee: Progenity, Inc., San Diego, CA (US)

( * ) Notice: Subject to any disclaimer, the term of this patent is extended or adjusted under 35 U.S.C. 154(b) by 0 days.

(21) Appl. No.: 16/299,537

(22) Filed: Mar. 12, 2019

(65) Prior Publication Data

US 2019/0282791 A1 Sep. 19, 2019

Related U.S. Application Data

(60) Provisional application No. 62/642,544, filed on Mar. 13, 2018.

(51) Int. Cl.
| | | |
|---|---|---|
| *A61M 31/00* | (2006.01) | |
| *A61B 10/00* | (2006.01) | |
| *A61B 10/02* | (2006.01) | |
| *A61B 5/00* | (2006.01) | |
| *A61K 9/00* | (2006.01) | |

(Continued)

(52) U.S. Cl.
CPC ............ *A61M 31/00* (2013.01); *A61B 1/041* (2013.01); *A61B 5/6861* (2013.01); *A61B 10/0045* (2013.01); *A61B 10/02* (2013.01); *A61B 10/04* (2013.01); *A61K 9/0009* (2013.01); *A61M 31/002* (2013.01); *A61B 2010/0061* (2013.01); *A61M 2205/0233* (2013.01);

(Continued)

(58) Field of Classification Search
CPC ............... A61M 31/00; A61M 31/002; A61M 2205/0233; A61M 2205/0238; A61M 2205/3334; A61M 2205/8218; A61B 5/6861; A61B 10/0045; A61B 10/02; A61B 10/04; A61B 2010/0061; A61K 9/0009; F03G 1/00; F03G 1/02; F03G 1/06

See application file for complete search history.

(56) References Cited

U.S. PATENT DOCUMENTS 3,797,492 A * 3/1974 Place ................... A61K 9/0004
604/890.1
4,507,115 A * 3/1985 Kambara ............ A61M 31/002
600/578

(Continued)

FOREIGN PATENT DOCUMENTS

| EP | 0061195 | 9/1982 |
| EP | 2016898 | 1/2009 |

(Continued)

OTHER PUBLICATIONS

International Search Report and Written Opinion in Application No. PCT/US2019/021814, dated Aug. 2, 2019, 24 pages.

(Continued)

*Primary Examiner* — James D Ponton
(74) *Attorney, Agent, or Firm* — Procopio Cory Hargreaves and Savitch LLP

(57) ABSTRACT

Ingestible devices with a relatively large payload volume or sample volume, as well as related components, systems and methods, are disclosed.

23 Claims, 18 Drawing Sheets

Figure 6

(51) Int. Cl.
*A61B 1/04* (2006.01)
*A61B 10/04* (2006.01)
(52) U.S. Cl.
CPC ............ *A61M 2205/0238* (2013.01); *A61M 2205/3334* (2013.01); *A61M 2205/8218* (2013.01)

(56) References Cited

U.S. PATENT DOCUMENTS

| | | | |
|---|---|---|---|
| 5,198,222 A | | 3/1993 | Scully et al. |
| 5,279,607 A | * | 1/1994 | Schentag ............ A61B 5/0031 604/114 |
| 6,245,057 B1 | | 6/2001 | Sieben |
| 6,349,232 B1 | * | 2/2002 | Gordon ................ A01K 27/009 604/20 |
| 2002/0173745 A1 | * | 11/2002 | Santini, Jr. .......... A61M 15/005 604/67 |
| 2004/0166140 A1 | * | 8/2004 | Santini, Jr. ........... A61K 9/0024 424/424 |
| 2005/0288594 A1 | * | 12/2005 | Lewkowicz ........... A61B 1/043 600/478 |
| 2008/0284599 A1 | * | 11/2008 | Zdeblick ................ A61B 5/076 340/572.1 |
| 2018/0052084 A1 | | 2/2018 | Jones et al. |
| 2018/0236173 A1 | * | 8/2018 | McCaffrey ........ A61M 5/14244 |

FOREIGN PATENT DOCUMENTS

| | | |
|---|---|---|
| WO | WO 2004026281 | 4/2004 |
| WO | WO 2004066903 | 8/2004 |
| WO | WO 2007004171 | 1/2007 |
| WO | WO 2014058605 | 4/2014 |
| WO | WO 2018050647 | 3/2018 |

OTHER PUBLICATIONS

PCT International Preliminary Report on Patentability in International Appln. No. PCT/US2019/021814, dated Sep. 24, 2020, 15 pages.
Invitation to Pay Additional Fees in International Application No. PCT/US2019/021814, dated May 24, 2019.

* cited by examiner

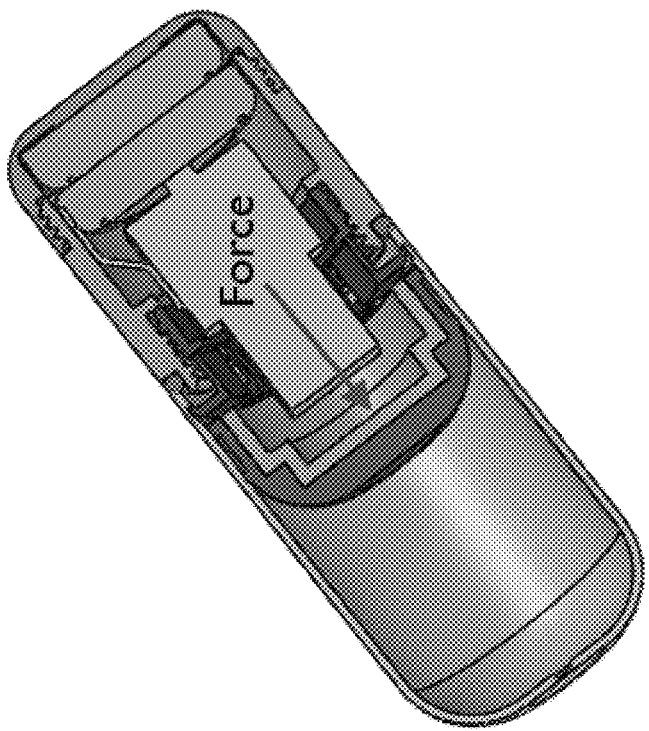
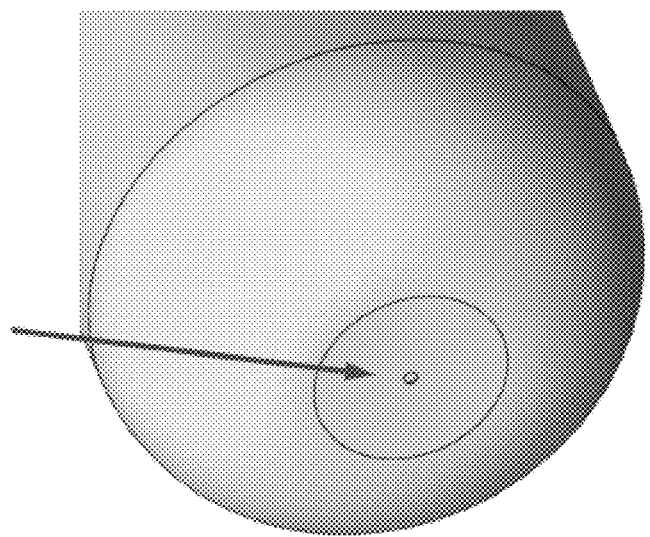
Figure 2

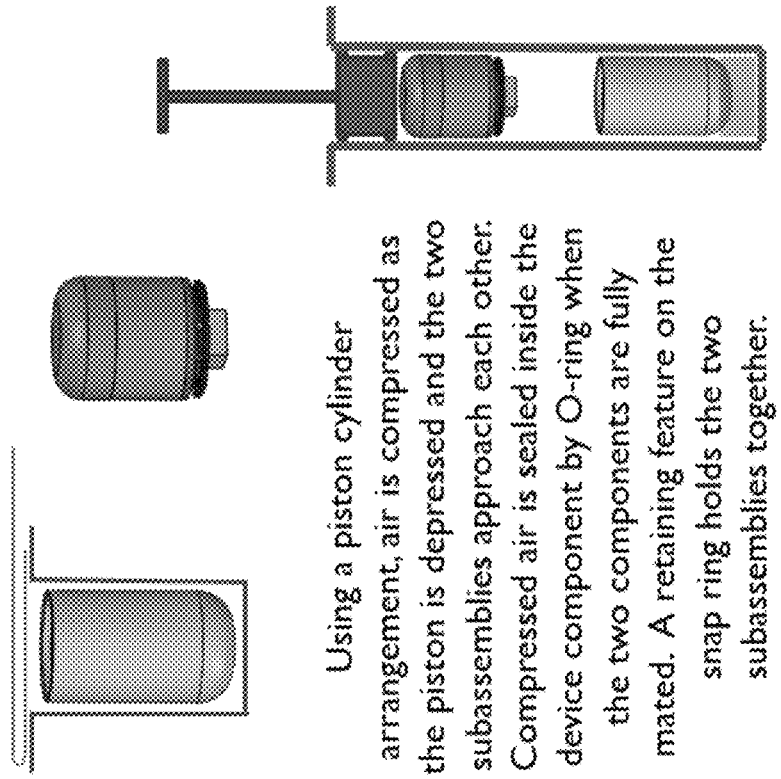
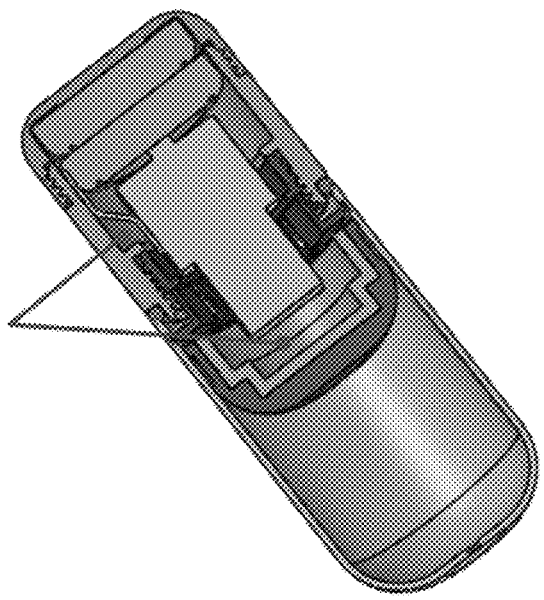

At the point of use, a drug container lid is removed and device component snapped into position.

Using a piston cylinder arrangement, air is compressed as the piston is depressed and the two subassemblies approach each other. Compressed air is sealed inside the device component by O-ring when the two components are fully mated. A retaining feature on the snap ring holds the two subassemblies together.

Compressed air throughout device compartment used to exert force on plunger

Figure 3

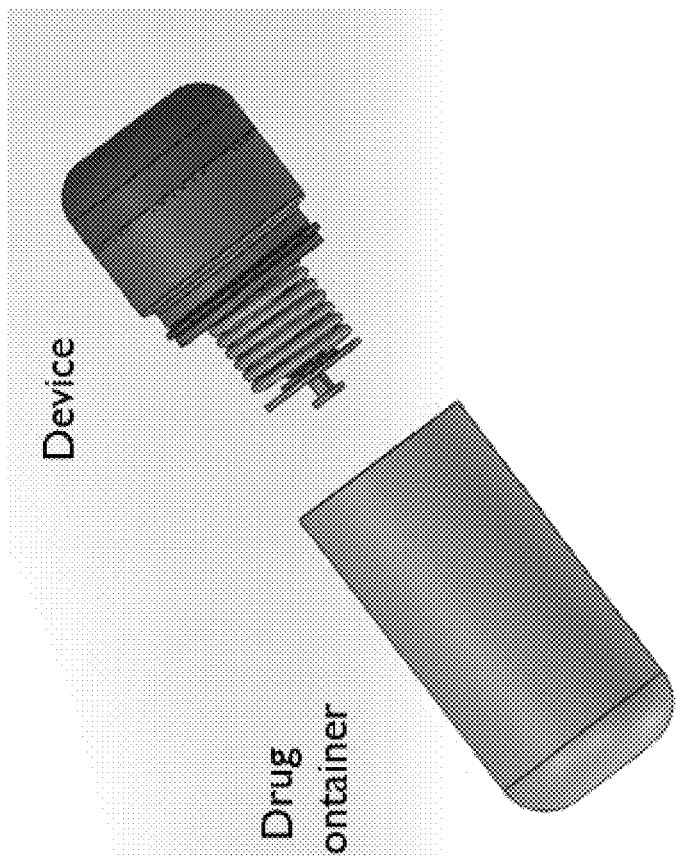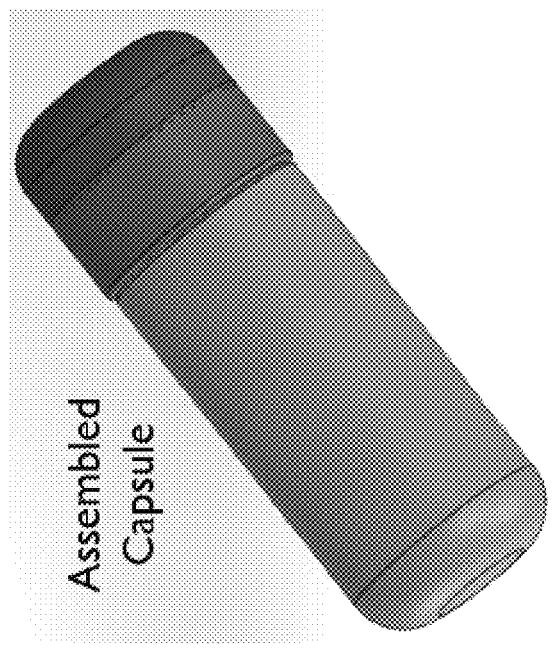
Figure 5

Window / Spring Retainer

- Injection molded from clear medical grade plastic
- .025" wall thickness in most areas
- May need relief between spring cavity and O-ring groove around portion of circumference

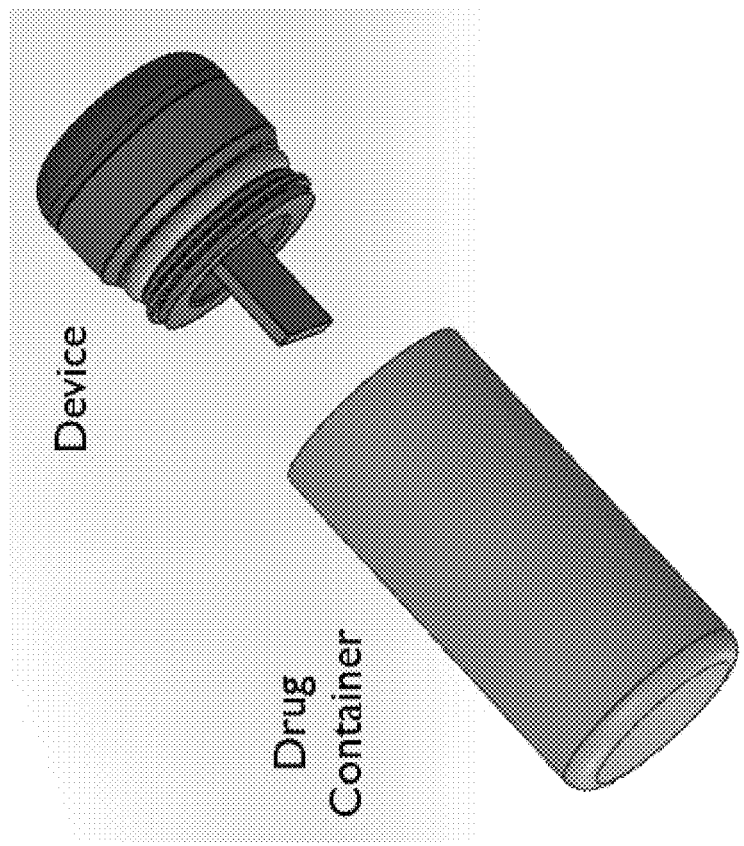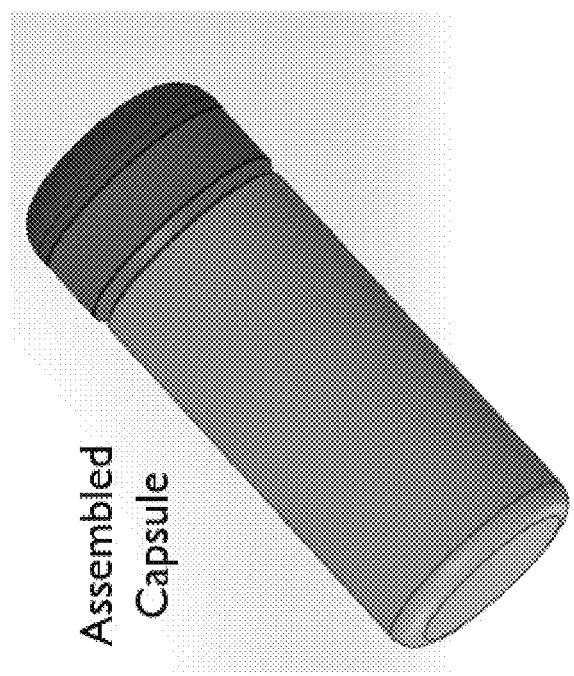
Figure 12

- Available with Flurotec coating
- Designed for 8.65mm ID barrel
- Threaded pusher rod cavity

Window / Insulator between anode and cathode

- Injection molded from clear medical grade plastic
- .025" wall thickness in most areas
- Hole for spring contact between anode and electronics (through C-clip)

INGESTIBLE DEVICE WITH RELATIVELY LARGE PAYLOAD VOLUME

CROSS-REFERENCE TO RELATED APPLICATION

The application claims priority to U.S. Patent Application Ser. No. 62/642,544 filed Mar. 13, 2018, entitled "Ingestible Device With Relatively Large Payload Volume", the entire contents of which is hereby incorporated by reference.

FIELD

The disclosure relates to ingestible devices with a relatively large payload volume, as well as related components, systems and methods.

BACKGROUND

It is known to use an ingestible device to try to deliver a substance, such as a drug, to the gastrointestinal (GI) tract of a subject.

SUMMARY

The disclosure provides an ingestible device with a novel, electrolytic mechanism for creating one or more openings in the ingestible device, wherein a substance can be dispensed through said opening, or a biological sample can be collected through the opening. The disclosure provides an ingestible device to dispense a substance (e.g., a drug, such as a drug containing one or more active pharmaceutical or biotherapeutic ingredients, a contrast agent, such as in preparation for an imaging procedure, or a probiotic) to one or more regions of the GI tract, such as, for example, the duodenum, the jejunum, the ileum, the cecum, or the colon. The ingestible device can exhibit highly targeted delivery of a substance to a desired location in the GI tract. In some embodiments, this is achieved by integrating a controllable valve for releasing the substance from the capsule as dictated by a localization scheme. The controllable valve can be formed via erosion (e.g., electrolytic erosion) of a portion (e.g., a portion of the housing) of the ingestible device.

The disclosure also provides an ingestible device to collect a substance (e.g., a biological sample from the GI tract) from one or more regions of the GI tract, such as, for example, the duodenum, the jejunum, the ileum, the cecum, or the colon. The ingestible device can exhibit highly targeted sampling of a biological sample from a desired location in the GI tract. In some embodiments, this is achieved by integrating a controllable valve for sampling a biological sample from the GI tract as dictated by a localization scheme. The controllable valve can be formed via erosion (e.g., electrolytic erosion) of a portion (e.g., a portion of the housing) of the ingestible device. The biological sample can enter the ingestible device by one or more passive or active motive forces, for example, via absorption, a mechanical mechanism, or a pressure difference (e.g., a sampling chamber is at a relatively lower pressure as compared to external pressure).

As referred to herein, the term "payload volume" is the volume of an ingestible device that contains, or is configured to contain, the one or more substances to be delivered by the ingestible device.

As used herein, the term "sample volume" is the volume of sample to be collected by the ingestible device, wherein a biological sample enters a sampling chamber in the ingestible device.

In some embodiments, an ingestible device can have a relatively large ratio of payload volume to total volume, or sample volume to total volume. Thus, for a given amount of substance to deliver, the device can be relatively small. Additionally or alternatively, for a given total volume, the ingestible device can house and/or deliver a relatively large amount of sub stance.

The disclosure provides technology that can treat GI conditions, such as a variety of inflammatory bowel disease (e.g., Crohn's disease, ulcerative colitis) via targeted delivery in close proximity to the diseased tissue. This can result in a locally higher concentration of the therapeutic agent and reducing systemic exposure throughout the body.

The disclosure provides technology that can, if desired, avoid systemic delivery of substances (e.g., one or more drugs) and any undesired side effects associated with systemic delivery.

In instances where systemic delivery is desired or intended, the disclosure provides technology that can yield enhanced systemic delivery via absorption at one or more predetermined locations in the GI tract. For example, the technology can be implemented to avoid exposure of the substance(s) to be delivered to be degraded by chemistry of the GI tract (e.g., by avoiding exposing the substance(s) to the relatively high acidity of the stomach).

In some embodiments, the ingestible device is appropriately sized to be relatively easy for a subject to swallow (e.g., for a subject having dysphagia). Such an ingestible device can also reduce or even eliminate undesired side effects (e.g., pain, esophagitis, gagging, choking, aspiration). In some embodiments, the ingestible device is appropriately sized to reduce risk of the device not passing through the entirety of the GI tract (e.g., the device becoming blocked at a gastrointestinal stricture).

In certain embodiments, a relatively small ingestible device is achieved by having items other than the substance(s) to be delivered or the sampling chamber occupy a relatively small proportion of the volume of the device. This can be achieved, for example, by having a controllable valve and motive force for releasing the substance(s) that occupy a small volume.

In some embodiments, the drug container is packaged separately or in a co-package. Optionally, the drug container and the device components can be brought together at the time of use or shortly before the time of use. Optionally, the joining of drug container with device components can be aided by an accessory device that can enhance the ease of use and/or reduce the likelihood of one or more use errors. In certain embodiments, the technology is compatible with commercial drug filling equipment, which can lead to enhanced ease of manufacture.

In some embodiments, the sampling chamber comprises sample preservatives, for example, as described in U.S. Ser. No. 15/680,430, entitled "SAMPLING SYSTEMS AND RELATED MATERIALS AND METHODS," and filed Aug. 18, 2017.

In one general aspect, the disclosure provides an ingestible device that includes a housing. The ingestible device has a total volume and a second volume selected from the group consisting of a payload volume and a sample volume. The ratio of the second volume to the total volume is at least 0.1.

In one general aspect, the disclosure provides an ingestible device including a housing that includes first and second components. The first component defines an anode, and the second component defines a cathode. The ingestible device is configured so that, during use of the device, a portion of the anode electrolytically erodes to provide an opening through which a substance in the first component exits the ingestible device. In some embodiments, multiple openings are formed in a single device. In a related embodiment, the multiple openings are formed simultaneously, or in series.

In one general aspect, the disclosure provides an ingestible device that includes a housing configured so that, during use of the ingestible device, an opening is formed in a housing of the ingestible device to allow a substance in the ingestible device to exit the ingestible device, or to allow a substance external to the ingestible device to enter the ingestible device, or both.

In some embodiments, an ingestible has a total volume and a second volume selected from the group consisting of a payload volume and a sample volume, and a ratio of second volume to the total volume is at least 0.1 (e.g., at least 0.15, at least 0.2, at least 0.25, at least 0.3, at least 0.35, at least 0.4, at least 0.45, at least 0.5).

In certain embodiments, the ingestible device is at least two millimeters (e.g., at least 5 millimeters, at least 10 millimeters, at least 15 millimeters, at least 20 millimeters, at least 25 millimeters, at least 30 millimeters, at least 35 millimeters, at least 40 millimeters, at least 45 millimeters, at least 50 millimeters) long.

In some embodiments, the ingestible device is at most 50 millimeters (e.g., at most 45 millimeters, at most 40 millimeters, at most 35 millimeters, at most 30 millimeters, at most 25 millimeters, at most 20 millimeters, at most 15 millimeters, at most 10 millimeters, at most five millimeters) long.

In some embodiments, the second volume of the ingestible device is at least five (e.g., at least 25, at least 50, at least 75, at least 100, at least 200, at least 300, at least 400, at least 500) µL.

In certain embodiments, the second volume is at most 400 (e.g., at most 300, at most 200, at most 100, at most 75, at most 50, at most 25) µL.

In some embodiments, the total volume of the ingestible device is at least 40 (e.g., at least 50, at least 75, at least 100, at least 200, at least 300, at least 400, at least 500, at least 600, at least 700, at least 800, at least 900, at least 1,000, at least 1,100, at least 1,200, at least 1,300, at least 1,400, at least 1,500, at least 1,600, at least 1,700, at least 1,800, at least 1,900, at least 2,000, at least 2,100, at least 2,200, at least 2,300, at least 2,400, at least 2,500) µL.

In certain embodiments, the total volume of the ingestible device is at most 2,500 (e.g., at most 2,400, at most 2,300, at most 2,200, at most 2,100, at most 2,000, at most 1,900, at most 1,800, at most 1,700, at most 1,600, at most 1,500, at most 1,400, at most 1,300, at most 1,200, at most 1,100, at most 1,000, at most 900, at most 800, at most 700, at most 600, at most 500, at most 400, at most 300, at most 200, at most 100, at most 75, at most 50) µL.

In some embodiments, the housing includes a first component and a second component. The first component can define the second volume. The second component can include a mechanism to propel a substance out of the first component, and/or the second component can include a mechanism to allow a substance to enter the first component. The mechanism can be configured to apply a mechanical force to the substance. The mechanism can be configured to apply gas pressure to the substance. The mechanism can include at least one spring configured to propel the substance out of the first component. The mechanism can include at least two different springs. The mechanism can include at least three different springs. The springs can be nested. A second spring can be nested between first and third springs, and a winding of the second spring can in a direction opposite to a winding of the first and third springs. The mechanism can include a gas generating device. The gas generating device can include a hydrogen source generated from electrically controlled chemical reaction.

In some embodiments, the ingestible device, further includes a window to pass light.

In certain embodiments, the ingestible device further includes at least one light source and at least one light detector. The light source and the light detector can be configured to determine the location of the ingestible device within the GI tract.

The first compartment can include an anode, and the second compartment can include a cathode.

The first compartment can include an exposed conductive surface. An area of the exposed conductive surface is at most $0.5$ mm$^2$, and/or at least $0.1$ mm$^2$.

A thickness of the conductive material at the exposed conductive surface can be at most 0.5 mm thick, and/or at least 0.1 mm thick.

The ingestible device can further include an insulating coating on the first compartment in an area adjacent the exposed conductive surface.

The ingestible device can further include a mechanism configured to bias the exposed conductive surface with a positive voltage relative to the cathode. The positive bias can be sufficient so that the exposed conductive surface electrolytically erode. Erosion of the exposed conductive surface can result in formation of an opening through which substance can exit the first compartment. the exposed conductive surface can be on an exterior of the ingestible device. The exposed conductive surface can be on an interior of the ingestible device.

The ingestible device can further include a coating to enhance wettability.

The ingestible device can further include an enteric coating.

The anode and the cathode may not be at opposite ends of the ingestible device.

In one general aspect, the disclosure provides a kit that includes a first compartment and a second compartment. The kit is configured so that, when the first and second compartments are joined, the result is an ingestible device as disclosed herein.

BRIEF DESCRIPTION OF THE DRAWINGS

Aspects of the technology are provided below in conjunction with the figures, in which:

FIG. 2 shows views of an ingestible device;
FIG. 3 shows views of an ingestible device and associated technology;
FIGS. 5-11 show an ingestible device with spring propulsion;
FIGS. 12-17 show an ingestible device with air pressure propulsion.

DETAILED DESCRIPTION OF EXEMPLARY EMBODIMENTS

Figure 1:
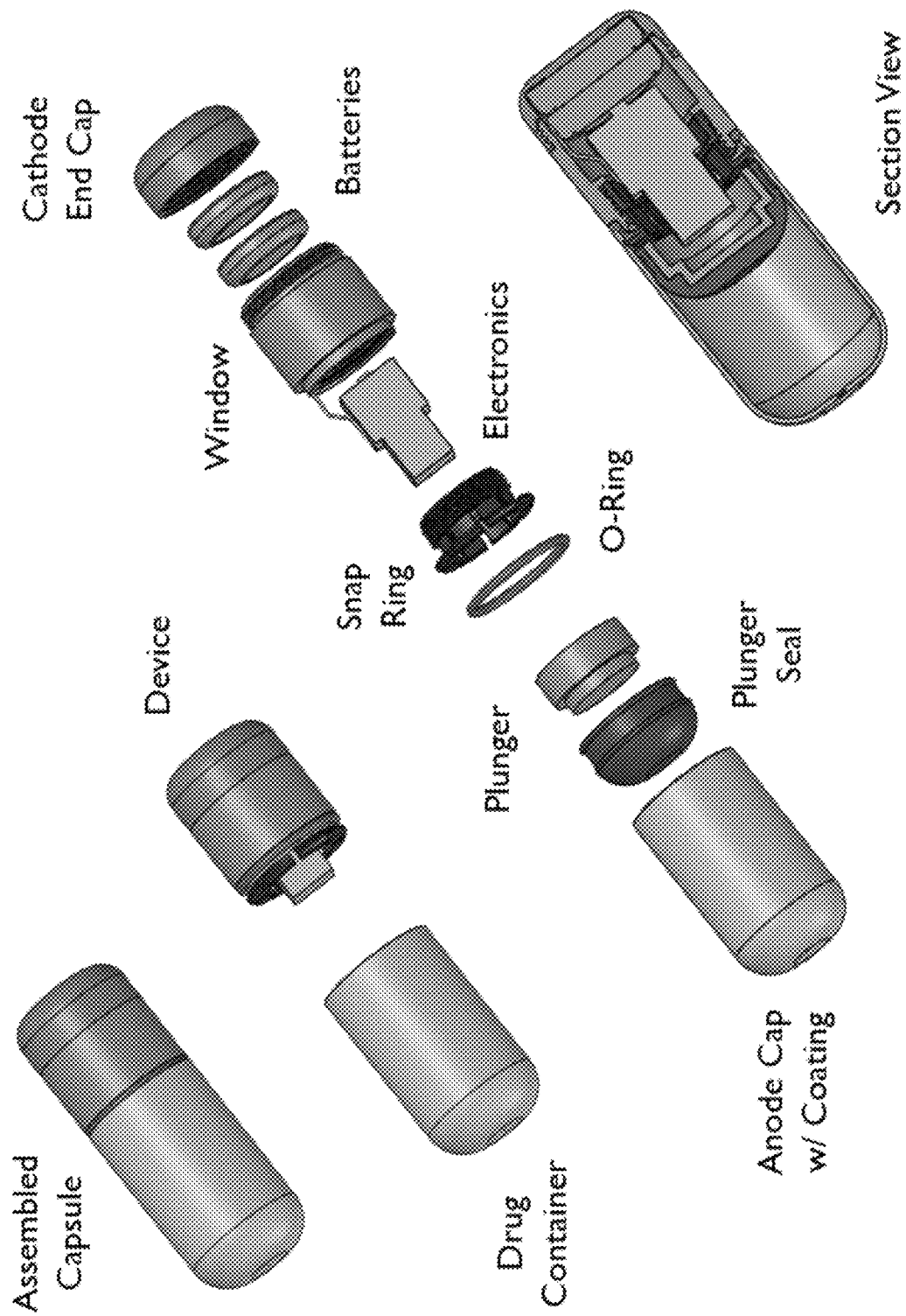
FIG. 1 shows views of an ingestible device.

Various exemplary embodiments of an ingestible device are disclosed herein. In general, unless otherwise indicated, it is to be understood of any aspect of a given embodiment can be combined with one or more aspects of one or more other embodiments.

The term "gastrointestinal tract" or "GI tract" refers to all portions of an organ system responsible for consuming and digesting foodstuffs, absorbing nutrients, and expelling waste. This includes orifices and organs such as the mouth, throat, esophagus, stomach, small intestine, large intestine, rectum, anus, and the like, as well as the various passageways and sphincters connecting the aforementioned parts.

An ingestible device can be used to treat a disease or disorder of the GI tract. Examples include inflammatory bowel disease (IBD), Crohn's disease (e.g., active Crohn's disease, refractory Crohn's disease, or fistulizing Crohn's disease), ulcerative colitis, indeterminate colitis, infectious colitis, microscopic colitis, drug or chemical-induced colitis, diverticulitis, ischemic colitis, pseudomembranous colitis, hemorrhagic colitis, hemolytic-uremic syndrome colitis, collagenous colitis, colitis associated with disorders of innate immunity as in leukocyte adhesion deficiency-1, diversion colitis, gastritis, peptic ulcers, stress ulcers, bleeding ulcers, gastric hyperacidity, dyspepsia, gastroparesis, Zollinger-Ellison syndrome, gastroesophageal reflux disease, short-bowel (anastomosis) syndrome, mucositis (e.g., oral mucositis, gastrointestinal mucositis, nasal mucositis and proctitis), necrotizing enterocolitis, esophagitis, a hypersecretory state associated with systemic mastocytosis, basophilic leukemia, hyperhistaminemia, Celiac disease (e.g., nontropical Sprue), enteropathy associated with seronegative arthropathies, eosinophilic gastroenteritis, colitis associated with radiotherapy or chemotherapy (such as checkpoint inhibitor chemotherapy), colitis associated with disorders of innate immunity such as leukocyte adhesion deficiency-1, gastritis, chronic granulomatous disease, food allergies, infectious gastritis or enterocolitis (e.g., *Helicobacter pylori*-infected chronic active gastritis), other forms of gastrointestinal inflammation caused by an infectious agent, irritable colon syndrome, small intestinal bacterial overgrowth (SIBO) and pouchitis.

In some embodiments, the substance contained in the ingestible device to be delivered in the GI tract is a drug. The disclosure is not limited in terms of the drug. For example, the drug can be a small molecule or a biologic. The disclosure also is not limited in terms of the condition sought to be treated by the drug. For example, the condition may be a GI tract disorder or not. In some embodiments, a drug is an analgesic drug, an antibiotic drug, an anticoagulant drug, an antidepressant drug, an anticancer drug, an antiepileptic drug, an anti-inflammatory drug (nonsteroidal anti-inflammatory drug, steroidal anti-inflammatory drug), an antipsychotic drug, an antiviral drug, a sedative drug, and/or an antidiabetic drug. Optionally, the ingestible device can contain more than one drug. In some embodiments, the drug is designed to treat a condition of the GI tract. In some embodiments, a drug is a TNFα inhibitor. In some embodiments, a drug is a IL-12/IL-23 inhibitor. In some embodiments, a drug is an IL-6R inhibitor. In some embodiments, a drug is an integrin inhibitor. In some embodiments, the TLR agonist specifically binds and activates TLR3 (e.g., a synthetic agonist). In some embodiments, a drug is a TLR agonist that specifically binds to and activates TLR4. In some embodiments, a drug is a TLR agonist that binds and activates TLR5. In some embodiments, a drug is a TLR agonist that binds and activates TLR7/8 (e.g., TLR7 agonist, TLR8 agonist, or a TLR7 and TLR8 agonist). In some embodiments, a drug is a TLR agonist that binds and activates TLR9. In some embodiments, the TLR9 agonist is a synthetic oligonucleotide. In some embodiments, a drug is a TLR agonist that is a bacterial or viral component. In some embodiments, a drug is a SMAD7 inhibitor. In some embodiments, a drug is a JAK inhibitor. In some embodiments, a drug is a low molecular weight immunosuppressant (L-M immunosuppressant). In some embodiments, a drug is an mTOR inhibitor. The drugs can be disposed within the same housing of the device or in separate housings of the device.

In some embodiments, an ingestible device can have a relatively large ratio of its payload volume or sample volume to its total volume. Various values for this ratio are disclosed elsewhere herein.

In certain embodiments, an ingestible device has certain dimensions (e.g., length, diameter, volume). Various values for these dimensions are disclosed elsewhere herein.

FIG. 1 shows an orally ingestible device (e.g., for the targeted delivery of one or more substances, such as active pharmaceutical ingredients) includes of a drug container and device components. The drug container includes an electrolytically erodible valve for opening the drug container at a desired location in the gastrointestinal tract. The casing of the drug container includes an exposed metal surface that acts as a valve to open the drug container to its surrounding environment. The exposed metal anode material acting as valve can include a metal alloy or substantially pure metal that is acceptable for human ingestion from consideration of its biocompatibility in the amounts electrolyzed during opening of the valve. A further desirable attribute, though not necessarily required, is that the metal be compatible with the drug product over long duration of storage. A wide variety of stainless steel alloys satisfy these criteria including SAE grades 303, 304, 304L, 316, 316L, 440. From consideration of nickel content, purity, and/or traceability, it may be desirable to choose from stainless steel grades approved for use as surgical implant materials including ASTM grades F138, F1314, F1586, F2229, or F2581. If the exposed area of metal to the drug is small, a variety of other materials of construction may be used that may have advantages for manufacturability such as nickel, cobalt nickel alloy, or plain steel.

FIG. 2 shows that the exposed metal surface is on the outer surface of the drug container and can be quite small relative to the total surface area of the drug container. At the time of valve actuation, the metal portion of the drug container is biased with a positive voltage relative to a metal cathode element. The bias is provided by the batteries (power supply). In the case of an external electrolytic circuit (electrolytically erodible surface being on the exterior of the device as shown in FIG. 1), the surrounding gastric fluids are the electrolyte that completes an electrolytic circuit between anode and cathode. With sufficient bias voltage (e.g., 1.5-15 volts, such as 3-5 volts), the anode will dissolve or erode electrolytically and thus open the drug formulation to its surrounding environment within a desired time interval. The appropriate bias voltage depends upon the chosen anode and cathode materials, cathode area relative to anode area, proximity of the cathode to anode, and desired performance. Increased voltage typically increases the rate of metal erosion unless bubbles are created that insulate the exposed metal from surrounding electrolyte. The voltage is chosen to be high enough such that electrolytic erosion occurs within an acceptable time without being so high that excessive bubbling occurs at the anode. Pulsing the DC voltage applied between anode and cathode can help reduce the amount of bubbling at the anode and make the electrolytic erosion process faster and/or more reliable. In the case of using pulsed DC voltage, frequency of pulsing can be in the range 5 to 500 hz, with 50 hz found experimentally to give good results. Duty cycle of the pulsed DC voltage relates to the percentage of time that the voltage is applied between anode and cathode, with the remainder of the time the applied voltage is at or near zero. An effective duty cycle for the purpose of making the electrolytic erosion process faster and/or more reliable is in the range 20% or 80% with 50% found experimentally to give good results.

Keeping the area of exposed metal on the drug container small can reduce the volume of metal to be electrolyzed, which can be desirable (e.g., in terms of biological exposure to the patient), and can reduce the total current required to open the valve. In some embodiments, the area is from 0.01 $mm^2$ to 0.20 $mm^2$. As an example, the area of the exposed metal can be 0.03 $mm^2$, and/or the drug container can have a diameter of 8.5 mm and a length of 14 mm. Other dimensions for the area of exposed metal that can be used are disclosed elsewhere herein.

Optionally, a nonconductive coating can be present on the metal drug container. Exemplary nonconductive coating materials include polyimide, poly(p-xylylene) polymer (trade name Parylene), polyurethane, PDMS (polydimethylsiloxane) or other silicone, polyester, polyamide, epoxy, Teflon or other fluoropolymer, polyethylene, polypropylene, acrylate polymer, polyvinylchloride, polyethylene vinyl acetate. In the case that the insulating material either does not adhere to the metal drug container, or the insulator is manufactured as a film, an adhesive can be incorporated between the insulator and metal drug container to join the two. The adhesive material can by one of the same family of polymers listed above. A relatively small area of the coating can be removed (e.g., by a mechanical mechanism or via laser ablation) to expose the metal, or a small area can be masked off prior to coating.

In some embodiments, external portions of the ingestible device are covered by one or more coatings that are sensitive to the environment. For example, some polymer coatings (e.g., enteric coatings) are pH-sensitive and respond by degrading at a selected pH. Thus, incorporating an environmentally-sensitive material to the device allows for an event (e.g., erode the valve, or actuate a force for dispensing a substance or collecting a sample) to be triggered once the ingestible device has encountered a target condition or a target location in vivo. In some embodiments a threshold sensor on the outside of the device could be present so that polymer erosion is sensed by a controlling electronics system which then starts the electrolysis circuit. In certain embodiments, a polymer piece is present between two electrodes with mechanical bias like a spring or shape memory so that, as the polymer erodes, the electrodes come into contact completing the electrolysis circuit. Such an approach can be implemented with reduced electronics (e.g., without a microcontroller). For example, the power could be provided by a battery or another power source with a relatively small volume.

Additionally or alternatively, the ingestible device may be configured to be targeted for the conditions associated with the colon, such as, for example, pH, enzymatic activity, and temperature.

In some embodiments, the ingestible device can include one or more coatings (e.g., one or more hydrophilic coatings) that can enhance wetting of the exterior of the device and therefore assist in completing the circuit (e.g., when fluid of the GI tract is the electrolytic fluid).

It can be desirable to have the thickness of metal in the valve area be small (e.g., to reduce the time and amount of current used to open the valve). For example, the metal portion of the drug container can be 0.025 mm thick across a diameter of 0.60 mm in the vicinity of the valve. In general, the thickness of the metal in the valve area can be in the range 0.002 mm to 0.200 mm. Other dimensions for the thickness of exposed metal that can be used are disclosed elsewhere herein.

Figure 4:
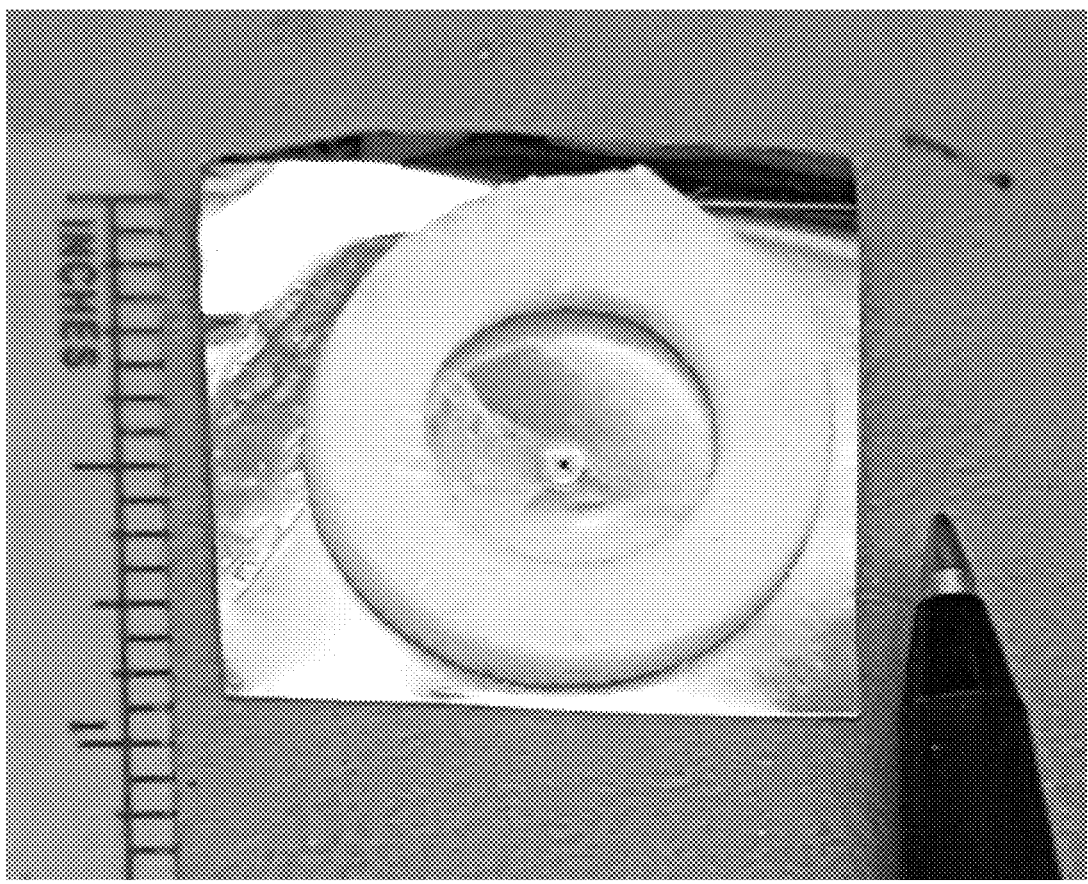
FIG. 4 shows an experimental result.

FIG. 4 shows the outcome of an experiment where 0.001 inch thick 316 stainless steel shim stock was insulated on one side by a 0.002 inch thick PET film with silicone adhesive except for a small 0.015 inch diameter hole that was drilled in the film prior to adhering to the shim stock. A cathode element was made of 24 gauge copper wire, and the electrolytic circuit was completed with the use of phosphate buffer solution as the electrolyte. The hole in the shim stock was created using approximately 5.0 volts for approximately one minute, during which time approximately two mA of current was flowing.

In some embodiments, the exposed metal surface can be on the inside of the drug container. In such embodiments, the cathode can be exposed to the drug formulation, and the drug formulation can be the electrolyte.

An electrical insulator is disposed between the cathode and the anode, to encourage the applied voltage to flow an ionic current through the electrolyte. In FIG. 1, the insulator is labeled as "Window." The window element can serve a dual purpose of electrically insulating the cathode from the anode while also providing optical transmission for a light-based localization system and method to determine the location of the device in the GI tract. Optionally, the information from the localization system/method can be used to determine when to actuate the valve and when to release the drug. A variety of localization systems/methods can be used. Such systems/methods can be based on one or more parameters, such as, for example, light measurements (e.g., changes in wavelength of absorbed and/or reflected light in the surrounding environment), time lapse (e.g., time since the ingestible device is swallowed, time since the ingestible device is known to pass a particular region of the GI tract), pH (e.g., via a pH meter associated with the ingestible device), imaging through the window, external imaging of the capsule through the body, changes in wavelength of absorbed and/or reflected light in the surrounding environment, and/or changes in the florescence of surrounding environment. Systems/methods for localization of an ingestible device via light measurements are disclosed, for example, in U.S. Ser. No. 62/540,873, entitled "LOCALIZATION SYSTEMS AND METHODS FOR AN INGESTIBLE DEVICE," and filed Aug. 3, 2017, and U.S. Ser. No. 15/514,413, entitled "ELECTROMECHANICAL PILL DEVICE WITH LOCALIZATION CAPABILITIES," and filed Mar. 24, 2017, the entire contents of each of which are incorporated by reference herein.

In some embodiments, the technology is configured to identify when the valve has been opened and when the applied voltage between anode and cathode can be terminated. For example, by superimposing an AC voltage between the anode and the cathode, or by alternating between applying DC voltage and then applying AC voltage, changes in capacitance between anode and cathode can be monitored. When the valve is closed, the exposed surface area on the anode is relatively small and the measured capacitance is relatively low. When the valve opens, the drug formulation becomes part of the electrolyte connecting the anode to the cathode. By exposing a relatively large area of metal on the inside of the drug compartment, the capacitance of the anode will increase when the valve opens. Monitoring and detecting when the capacitance increases can be used to indicate when the valve has opened. Alternatively or additionally, detecting when the valve is open and when the applied voltage can be terminated can rely on detected movement of the plunger. For the case of a motive force applied to the plunger, substance (e.g., one or more drugs) is expelled from the drug container when the valve opens and plunger will begin to translate. This translation can be detected by, for example, breaking or making an electrical contact as in the case of a mechanical switch. Optionally, an electrical contact can be associated with the plunger so that, as the plunger advances to the end position, the contact slides beyond a trace opening the circuit and stopping the reaction.

In some embodiments, it may be sufficient to allow passive diffusion as the mechanism for releasing substance form the drug container. In certain applications, it may be desirable to forcibly expel substance from the drug container. In such embodiments, a movable plunger can be used to apply pressure to the drug formulation to force drug through the open valve into its surrounding environment. The motive force for applying the pressure can be, for example, air pressure inside the capsule that is greater than ambient pressure, a spring (e.g., a coil spring, a spiral spring, a torsion spring operating through a lead screw), and/or a gas generating device such as, for example, a hydrogen source generated from an electrically controlled chemical reaction. The work energy to, for example, compress air or a spring may be applied at the time of assembly of the capsule, whether the capsule is assembled during manufacturing and prior to storage before use, or is assembled after storage and just prior to the point of use. Various approaches to generating a motive force to deliver a substance from an ingestible device are disclosed, for example, in U.S. Ser. No. 15/699,848, filed Sep. 8, 2017, and incorporated by reference herein in its entirety.

Figure 6:
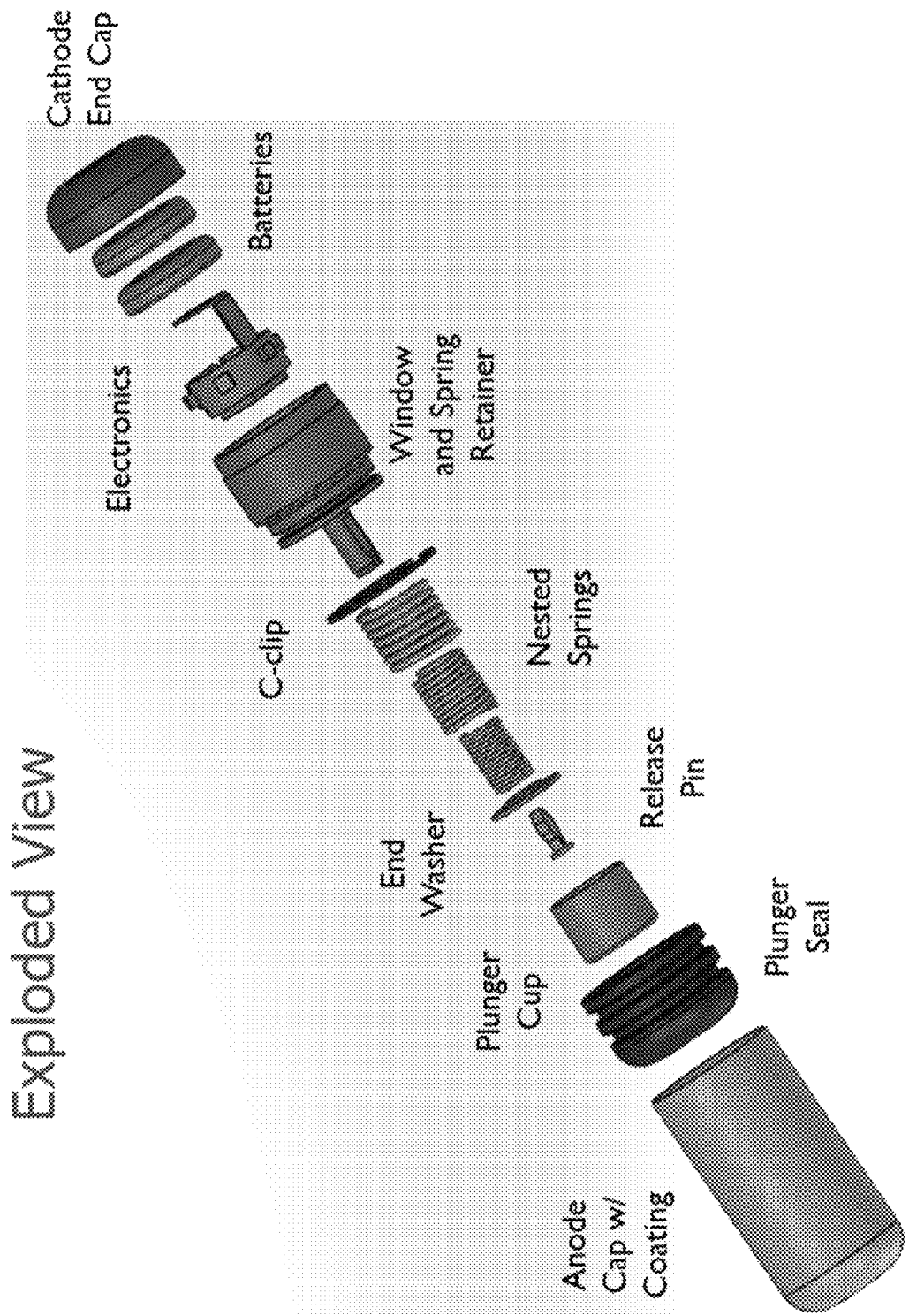
Figure 7:
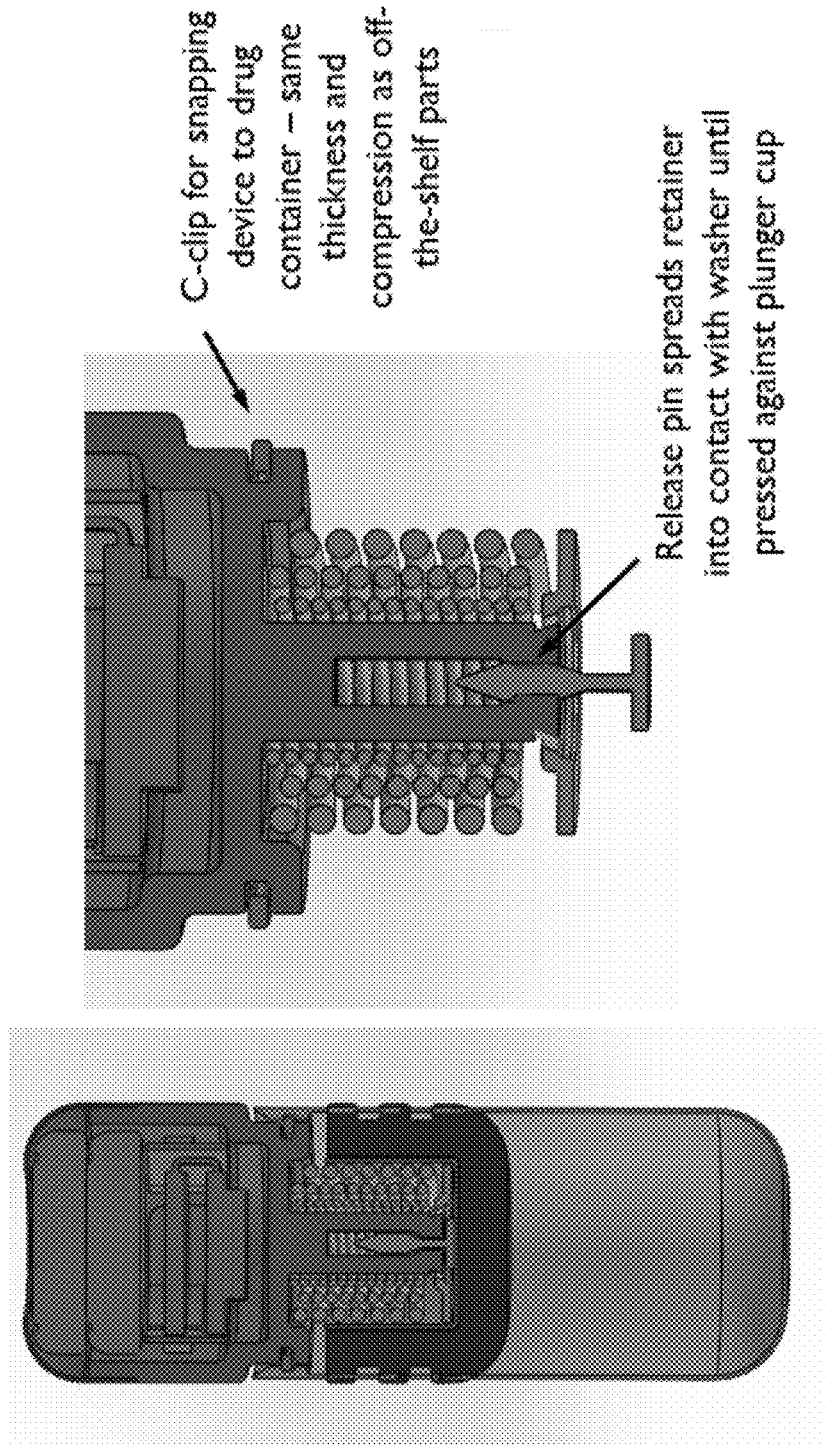
Figure 8:
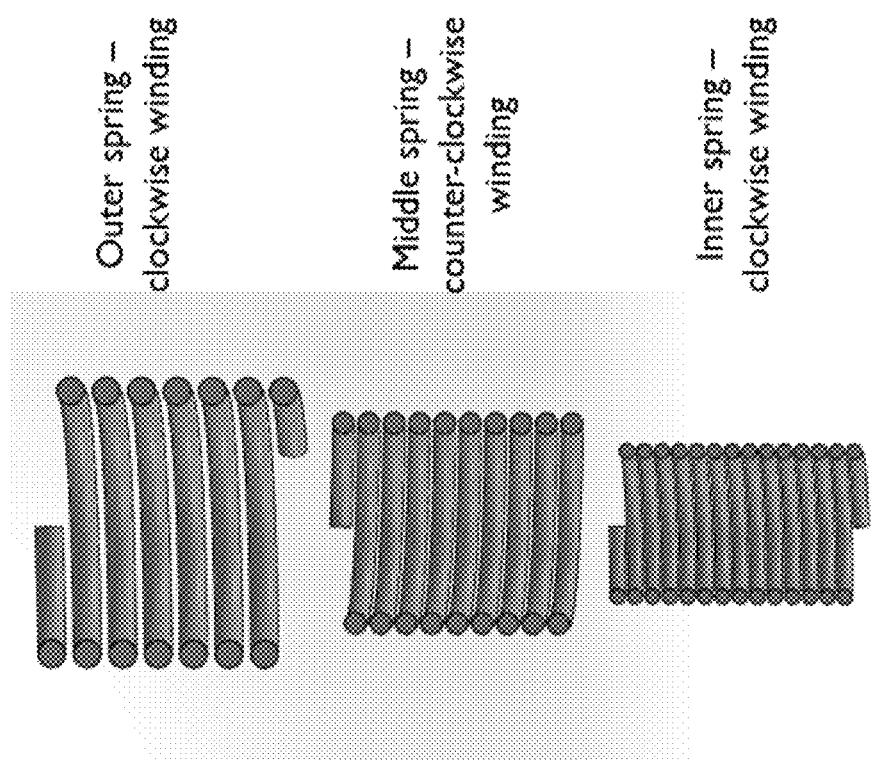
Figure 9:
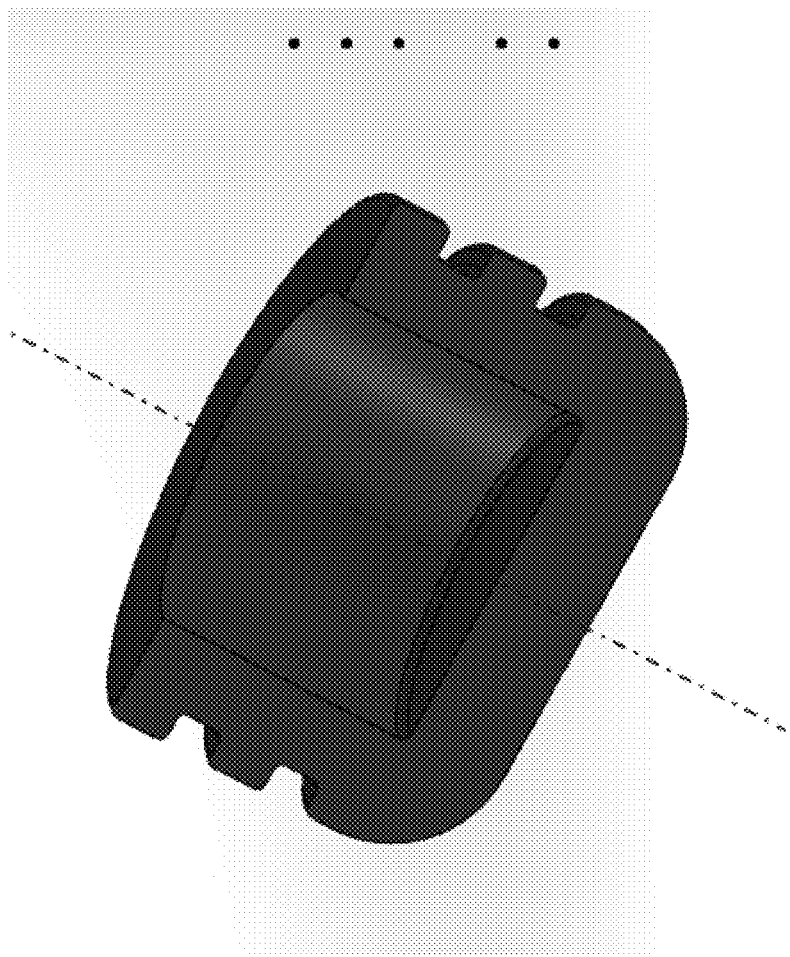
Figure 10:
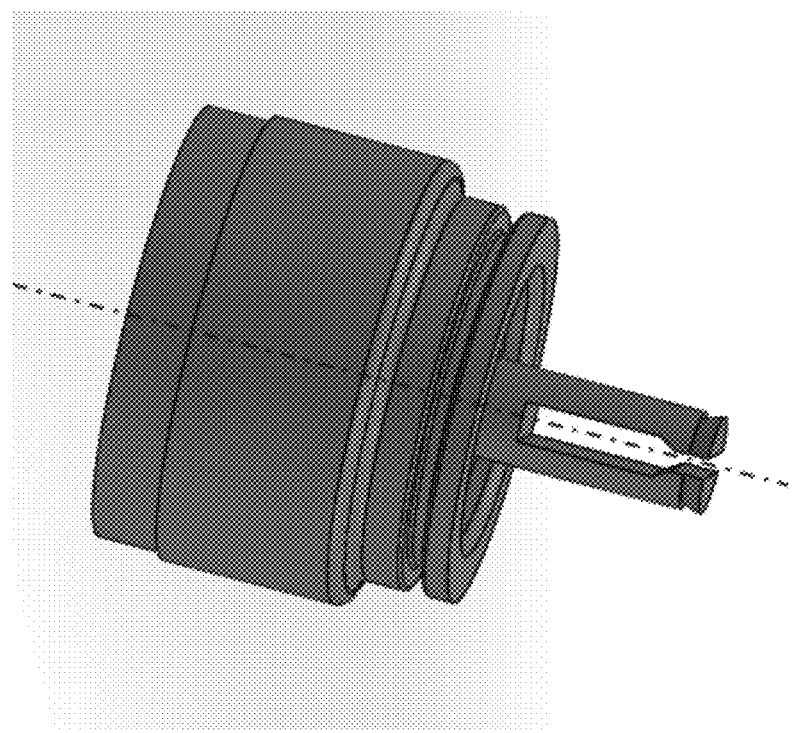
Figure 11:
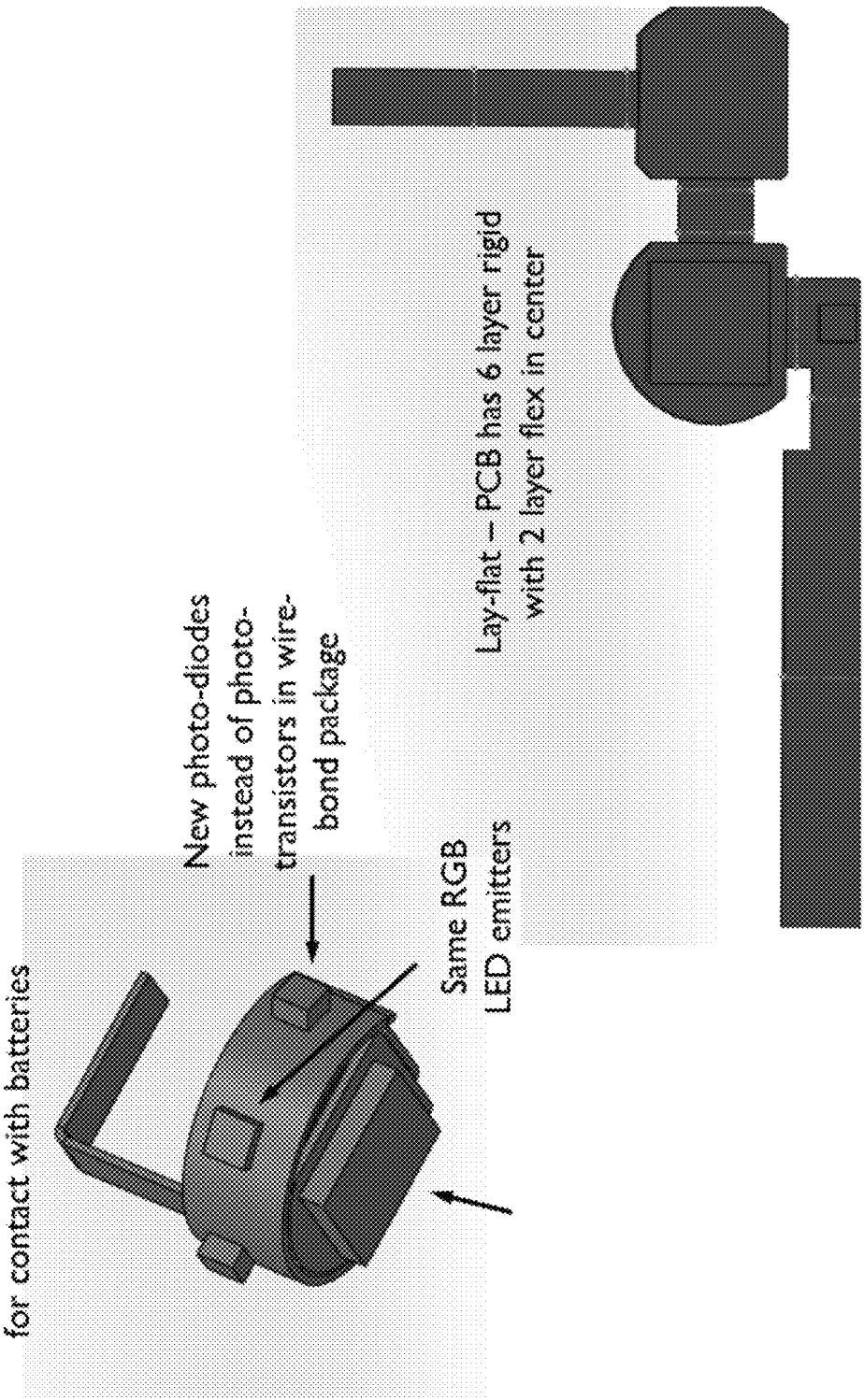

FIG. 5 shows views of an ingestible device that uses spring propulsion for substance delivery in its assembled and partially disassembled states. FIG. 6 shows an exploded view of the ingestible device including a coated anode cap, a plunger seal, a plunger cup, a release pin, an end washer, nested springs, a C-clip, a window and spring retainer, electronics, batteries and a cathode end cap. FIG. 7 shows views of the ingestible device with the springs retained in a compressed state (prior to use of the device to delivery one or more substances). FIG. 7 shows that the C-clip for snapping the drug container to the other portion of the device. Optionally, the C-clip can have the same thickness and compression as an off-the-shelf C-clip. FIG. 7 also shows that the release pin spreads the retainer into contact with the washer until pressed against the plunger cup. FIG. 8 shows the nested springs (outer spring with clockwise winding, middle spring with counter-clockwise winding, and inner spring with clockwise winding) to provide high energy density. All three springs can be designed for similar solid height, free length and peak stress. The guidance from the retainer shaft and the plunger cup can reduce the possibility of spring entanglement. The opposite winding direction of the middle coil can further reduce the possibility of entanglement. FIG. 9 shows the plunger seal, which can have a design similar to a commercial design with a few modifications, including being about 15% shorter. The plunger seal can have a similar radial compression, can be made from the same low permeability material, can have the same coating options as a commercial plunger seal. The pusher rod cavity can be a straight walled cylinder rather than threaded. FIG. 10 shows the window/retainer, which can be made from an injection molded material of clear medical grade plastic. The window/retainer may be 0.025 inch thick in most areas. A relief can be present between the spring cavity and the O-ring groove around a portion of the circumference. FIG. 11 shows views of the printed circuit board portion, which includes a flex tail that wraps around for contacting the batteries. It also includes light emitters (e.g., RGB LED emitters) and light detectors (e.g., photodiodes or phototransistors) for localization of the device in the GI tract.

Figure 13:
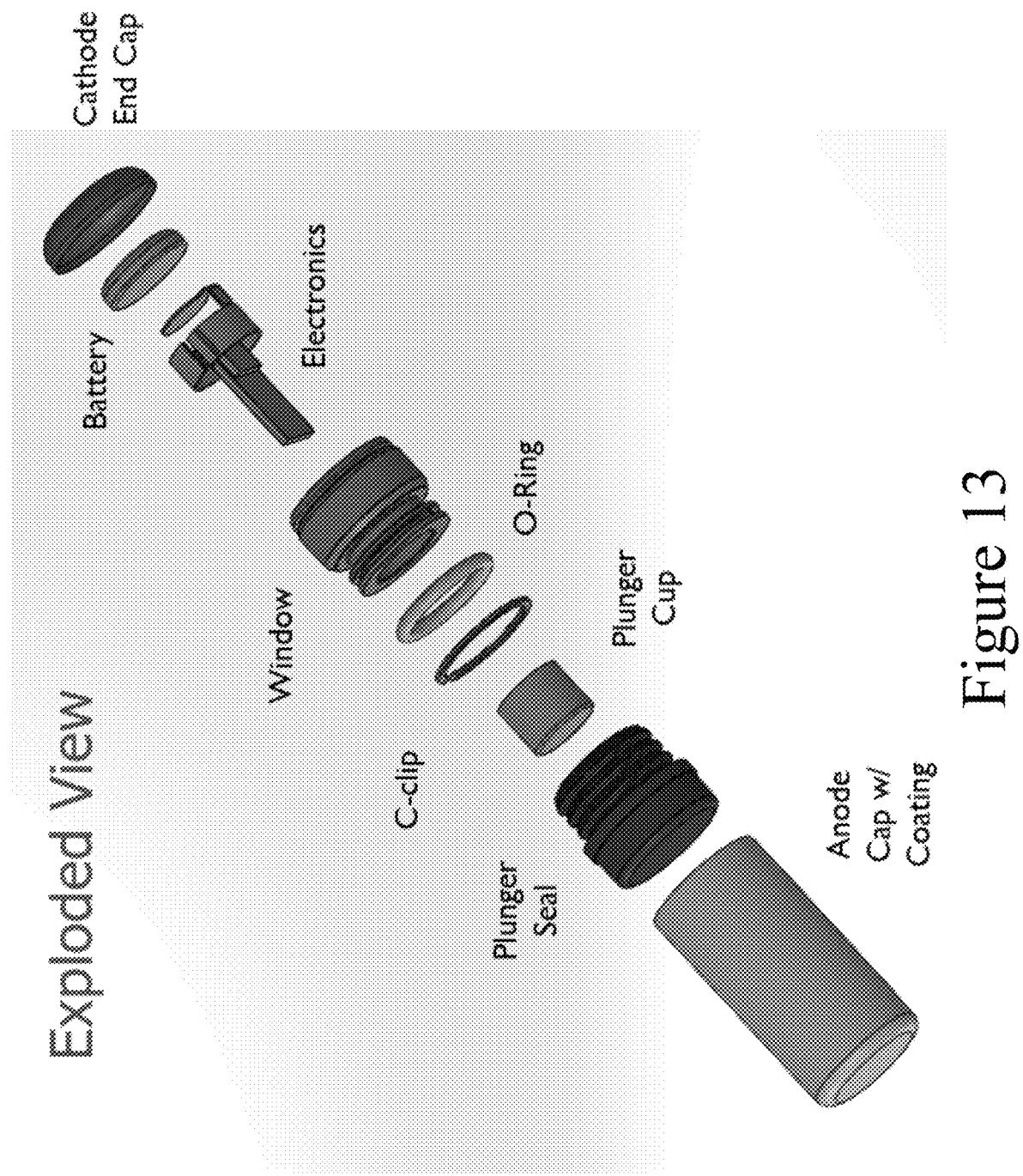
Figure 14:
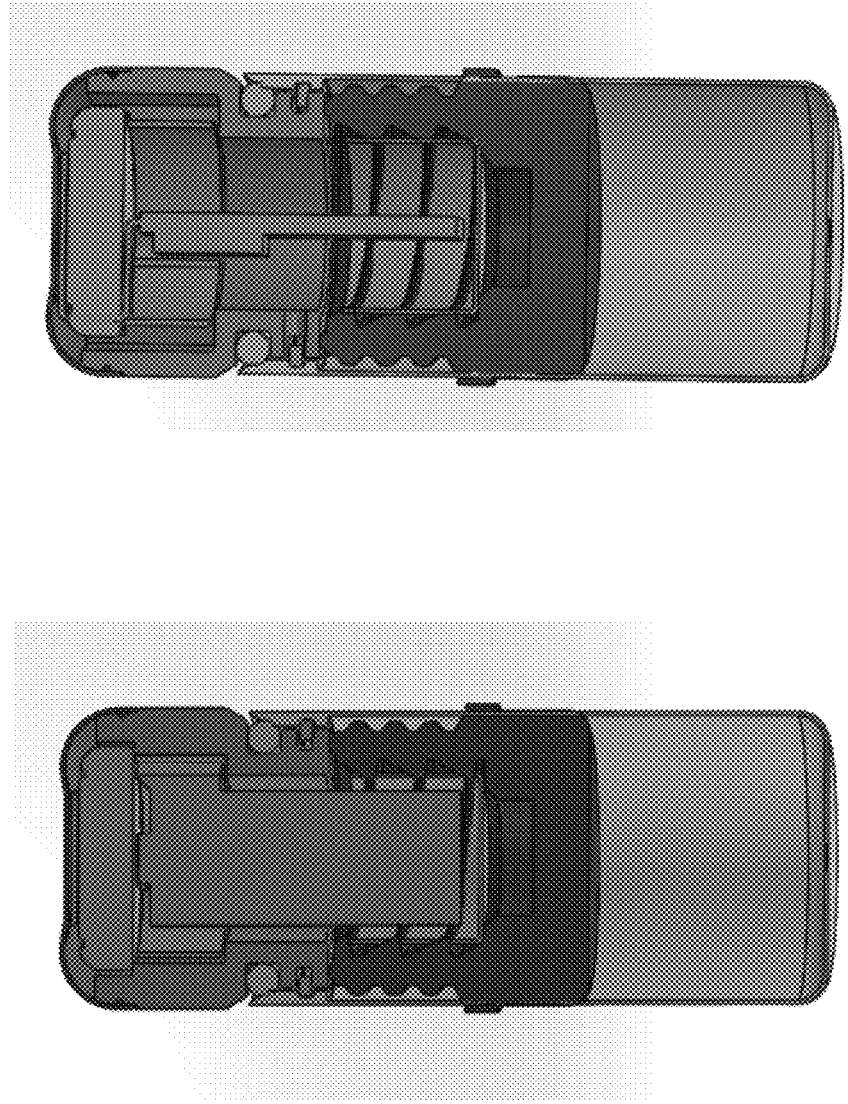
Figure 15:
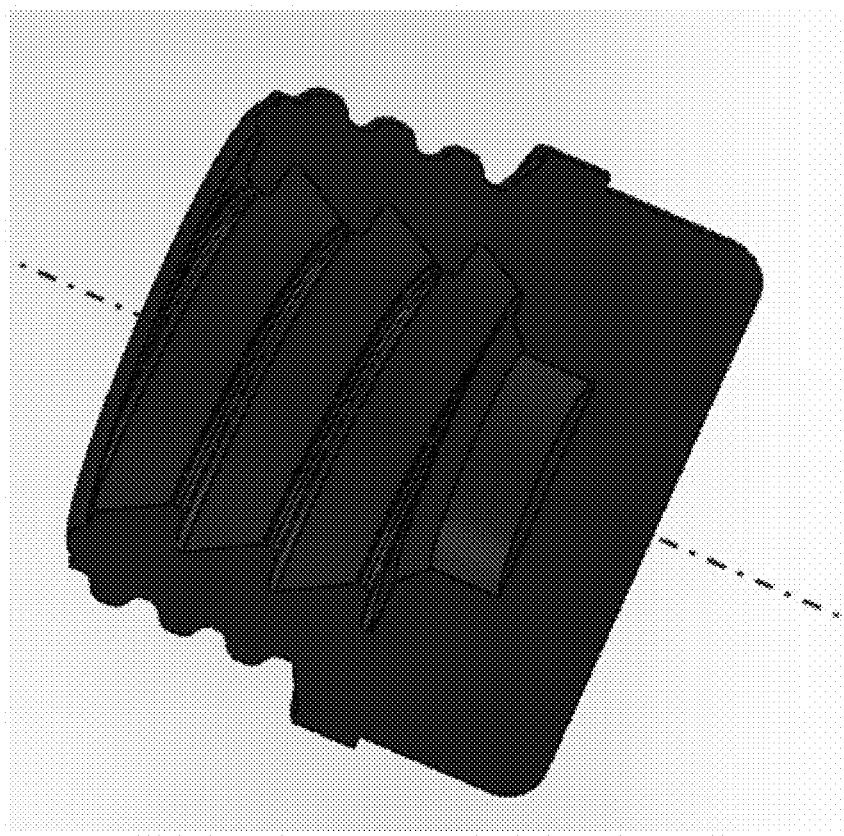
Figure 16:
Figure 17:
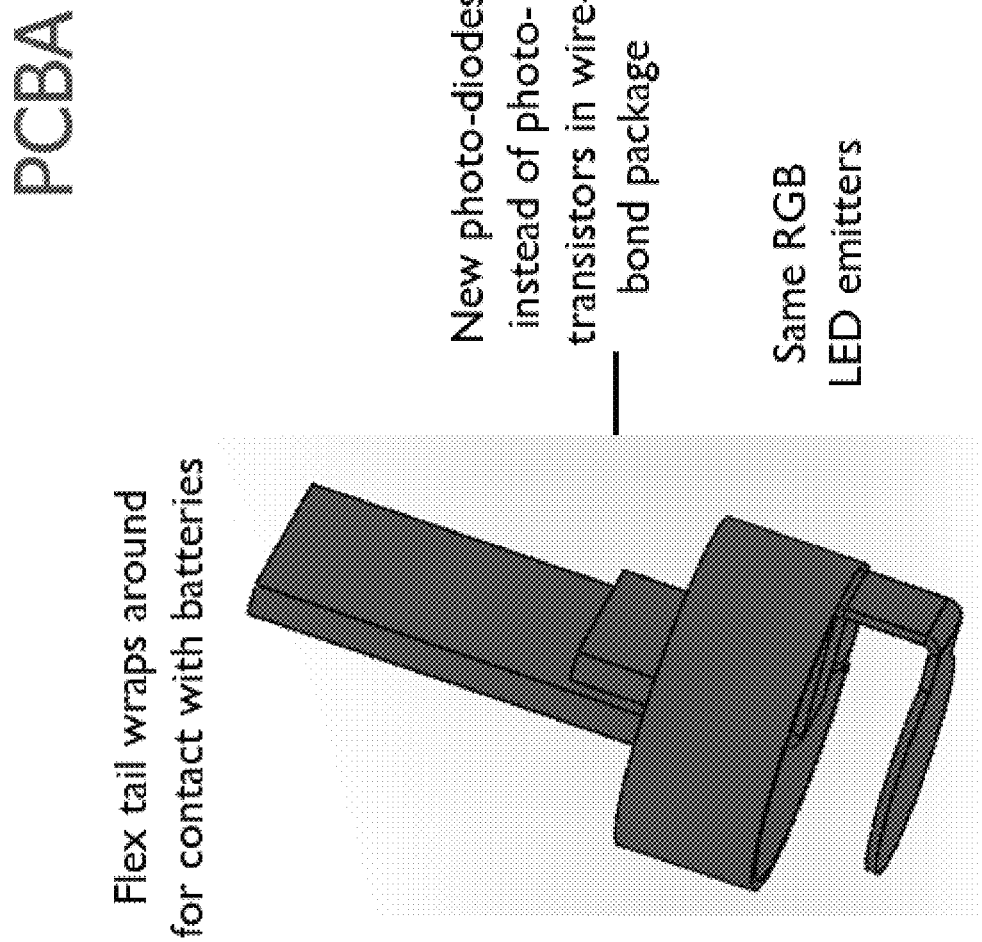

FIG. 12 shows views of an ingestible device that uses air pressure propulsion for substance delivery in its assembled and partially disassembled states. FIG. 13 shows an exploded view of the ingestible device including a coated anode cap, a plunger seal, a plunger cup, a C-clip, an O-ring, a window, electronics, batteries and a cathode end cap. FIG. 14 shows orthogonal section views of the device. FIG. 15 shows the plunger seal, which can be an off-the-shelf plunger seal which may have a Flurotec coating, an 8.65 mm inner diameter barrel, and a threaded pusher rod cavity. FIG. 16 shows the window/insulator, which can be made from an injection molded material of clear medical grade plastic. The window/insulator may be 0.025 inch thick in most areas, and can have a hole for a spring contact between the anode and the electronics (through the C-clip). FIG. 17 shows the printed circuit board portion, which includes a flex tail that wraps around for contacting the batteries. It also includes light emitters (e.g., RGB LED emitters) and light detectors (e.g., photodiodes or phototransistors) for localization of the device in the GI tract.

In certain embodiments, it may be desirable to have the drug container packaged separately from the device components, or co-packaged with the primary drug container separate from the device components. In such embodiments, final assembly of the capsule can be done at the time of use or shortly before the time of use.

In embodiments of separately packaged or co-packaged drug container and device components, an accessory device may be used to assist in assembly. For example, FIG. 3 shows an embodiment that involves using a piston and cylinder arrangement to compress air while bringing two subassemblies of the capsule together. As the air is compressed, the two subassemblies come together and are retained into mating position with a sealing O-ring in between that prevents compressed air in the capsule from leaking out. Work energy to drive this accessory device can be provided, for example, by user input and/or via a mechanical spring storing energy in the accessory device prior to use.

To assist in maintaining drug purity during storage and prior to use, the materials of construction for the drug container and valve are compatible with the drug formulation. The materials often have a history of being used in other commercial products, or are known to be acceptable for electrolytic reaction in the body. For example, grade 304 stainless steel, grade 316 stainless steel, and other metals with or without supplemental coatings. Such coatings may be applied to the inside and/or outside of the drug container surfaces in contact with the drug and body fluids. Plastic materials may be used for the drug container with a metal portion of the container where the valve is located. The plunger seal can be made from, for example, butyl type rubber, silicone rubber, or other pharmaceutical grade elastomer. Optionally, the drug container may include a lubricant and/or coating to reduce friction between the plunger and the interfacing surface of the drug container.

Figure 18:
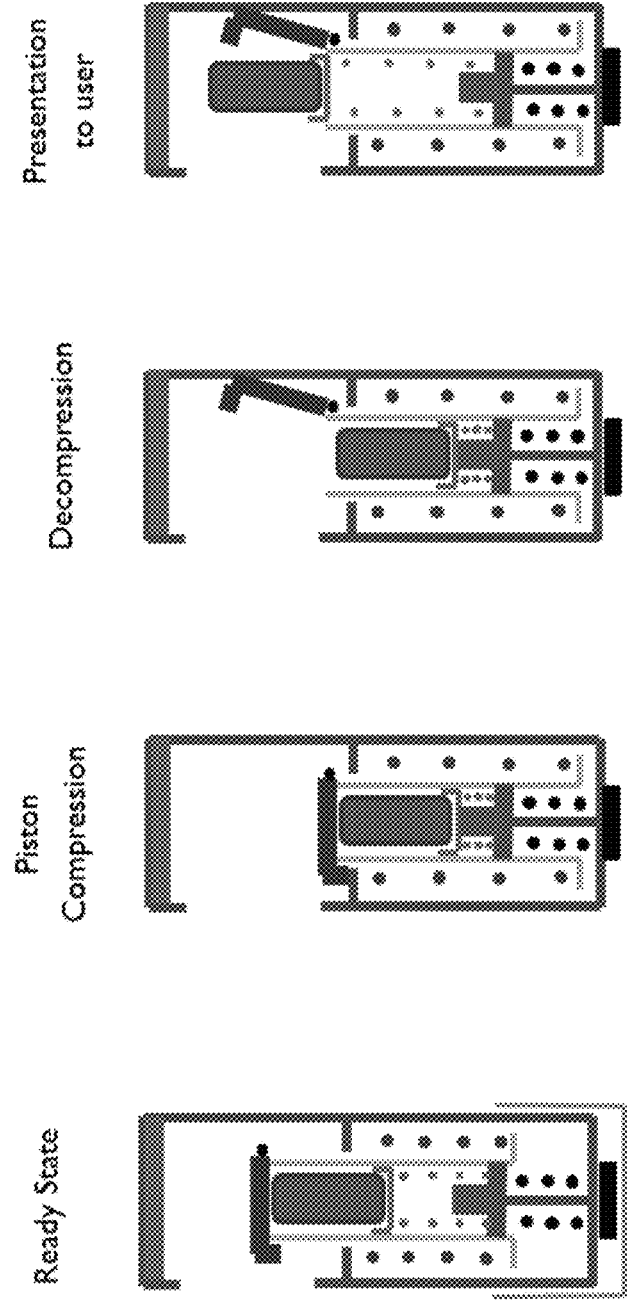
FIG. 18 shows a packaging concept.

FIG. 18 shows a pen-like compression mechanism for packaging. The figure shows the system in its ready state, piston compression state, decompression state and state for presentation to the use.

In another packaging concept, a cap is twisted to produce axial compression which mates the two halves together. A short stroke may be desirable. In such embodiments, a spring force may be preferred over gas pressure.

In a further packaging concept, a thread-like fiber releases the spring motive force (e.g., one or more springs) to pressurize the drug compartment. The fiber may be anchored to the packaging so that it is pulled from the device when removing the packaging prior to use.

In an additional packaging concept, a loop of packaging material is exposed on the exterior of an accessory that releases a spring to compress the device. In such embodiments, the motive force can be provided by gas pressure or spring force.

In still another packaging concept, multiple capsules are loaded in a single package that incorporates separate compartments (e.g., similar to a blister pack). Removing the cover to expose the device triggers a compression of the device.

In a further packaging concept, the primary container closure is defined by the drug container itself, and the device in mated proximity does not need to be included in drug stability testing.

In another packaging concept, the drug container is pressurized at the time of manufacture. For example, pressurization can be achieved via an inert gas, such as nitrogen or argon. In another packaging concept, the sampling chamber is pressurized at the time of manufacture such that it has a negative pressure. In another packaging concept, the sampling chamber comprises an absorptive material, which may further include an absorptive appendage designed to extend outside of the opening.

In a further packaging concept, gas pressure is sealed with the drug container sufficiently well to prevent pressure decay below an acceptable level over the shelf life of the device. Optionally, such a seal is not a hermetic seal.

In another concept, the drug container and device halves are combined during manufacture and ready for use.

Combinations of packaging approaches and concepts are possible.

While certain embodiments have been disclosed, the disclosure is not limited to such embodiments. Other embodiments are possible.

As an example, in some embodiments, the device is capable of collecting one or more samples (e.g., samples of fluid and/or tissue of the GI tract). Examples of systems and methods for such sample collection are disclosed, for example, in U.S. Ser. No. 14/460,893, entitled "INGESTIBLE MEDICAL DEVICE," and filed Aug. 15, 2014, and U.S. Ser. No. 15/680,400, entitled "SYSTEMS AND METHODS FOR OBTAINING SAMPLES USING INGESTIBLE DEVICES," and filed Aug. 18, 2017, the entire contents of each of which are incorporated by reference herein.

As another example, in some embodiments an anode is not an end cap of the device. For example, an anode can be an insert, such as a conductive (e.g., metal) disk.

As a further example, in certain embodiments, an anode and a cathode are not at opposite ends of the device. For example, a cathode trace can be patterned. Optionally, a cathode can be an insert, such as a conductive (e.g., metal) disk. The anode and cathode can be close proximity to each other. Optionally, a cathode could be a conductive ring surrounding the valve, which could potentially increase the chance for electrical circuit to be completed by wet environment outside the capsule.

As an additional example, while examples of triggering mechanisms have been disclosed, the disclosure is not limited to such triggering mechanisms. In general, the triggering mechanism can be any mechanism that would trigger the electronics system to initiate the electrolysis process. The triggering mechanism need not be run by a microprocessor and battery. As an example, as noted above, the triggering mechanism can involve the mechanical closing of a circuit contact. In another embodiment, the triggering mechanism may include a sensor, for example a threshold sensor, as described in WO2018050647, filed Sep. 12, 2017, which is hereby incorporated by reference. The sensor may be a threshold sensor, for example, of a type that includes an enteric polymer material deposited over electrodes. For example, the sensor, or a portion of the sensor, is disposed on an external surface of the housing. In use, a raised pH and aqueous environment may cause the enteric polymer to erode. This exposes the electrodes and this condition is used as an electrical switch. Note that the selection of polymer material, along with the possibility of layering different polymer materials, makes the switch sensitive to different pH environments and may be used to target different locations within the GI tract, for example.

As a further example, while certain embodiments of collecting a sample have been provided, the disclosure is not limited to such embodiments. For example, electrolytic erosion can trigger mechanical motion as described that could open and close a window or valve for sampling.

Other embodiments are covered by the claims.

What is claimed is:

1. An ingestible device, comprising:
    a housing comprising first and second components; and
    a mechanism in an interior of the housing,
    wherein:
        the first component defines an anode;
        the second component defines a cathode;
        the ingestible device is configured so that, during use of the device, a portion of the anode electrolytically erodes to provide an opening in the housing;
        the mechanism is configured to apply a mechanical force to a substance to propel the substance out of the housing via the opening;
        the mechanism comprises at least one spring configured to provide the mechanical force;
        the at least one spring comprises first, second and third springs;
        the second spring is nested between the first and third springs;
        a winding of the second spring runs in a direction opposite to a direction of a winding of the first spring; and
        a winding of the third spring runs in the same direction as the winding of the first spring.

2. The ingestible device of claim 1, wherein the ingestible device has a total volume and a second volume selected from the group consisting of a payload volume and a sample volume, and a ratio of second volume to the total volume is at least 0.1.

3. The ingestible device of claim 2, wherein the ratio of the second volume to the total volume is at least 0.2.

4. The ingestible device of claim 2, wherein the second volume of the ingestible device is at most 400 µL.

5. The ingestible device of claim 4, wherein the second volume of the ingestible device is at least five µL.

6. The ingestible device of claim 5, wherein the total volume of the ingestible device is at most 1,100 µL.

7. The ingestible device of claim 6, wherein the ingestible device is at least two millimeters long and at most 20 millimeters long.

8. The ingestible device of claim 7, wherein the first component comprises an exposed conductive surface, and an area of the exposed conductive surface is at most 0.1 mm$^2$.

9. The ingestible device of claim 8, wherein a thickness of a conductive material at the exposed conductive surface is at least 0.1 mm and at most 0.25 mm.

10. The ingestible device of claim 9, further comprising an enteric coating.

11. The ingestible device of claim 10, wherein the anode and the cathode are not at opposite ends of the ingestible device.

12. The ingestible device claim 2, wherein the total volume of the ingestible device is at most 1,100 μL.

13. The ingestible device of claim 1, wherein the ingestible device is at most 20 millimeters long.

14. The ingestible device of claim 13, wherein the device is at least two millimeters long.

15. The ingestible device of claim 1, wherein the first component comprises an exposed conductive surface.

16. The ingestible device of claim 15, wherein an area of the exposed conductive surface is at most 0.1 mm$^2$.

17. The ingestible device of claim 15, wherein a thickness of a conductive material at the exposed conductive surface is at most 0.25 mm.

18. The ingestible device of claim 17, wherein the thickness of the conductive material at the exposed conductive surface is at least 0.1 mm.

19. The ingestible device of claim 15, further comprising an insulating coating on the first component in an area adjacent the exposed conductive surface.

20. The ingestible device of claim 1, further comprising an enteric coating.

21. The ingestible device of claim 1, wherein the anode and the cathode are not at opposite ends of the ingestible device.

22. The ingestible device of claim 1, wherein the at least one spring comprises at least one member selected from the group consisting of a coil spring, a spiral spring and a torsion spring.

23. The ingestible device of claim 1, further comprising a plunger between the at least one spring and the substance so that the plunger transfers the mechanical force from the at least one spring to the substance.

* * * * *